United States Patent
Stempfer et al.

(10) Patent No.: US 8,055,476 B2
(45) Date of Patent: Nov. 8, 2011

(54) SYSTEM AND METHOD TO MINIMIZE DOWNTIMES OF MEDICAL APPARATUSES

(75) Inventors: Wolfgang Stempfer, Erlangen (DE); Ralph Thyroff, Stegaurach (DE); Matthias Unterdoerfer, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 432 days.

(21) Appl. No.: 12/264,964

(22) Filed: Nov. 5, 2008

(65) Prior Publication Data
US 2009/0119067 A1    May 7, 2009

(30) Foreign Application Priority Data
Nov. 5, 2007   (DE) .......................... 10 2007 053 048

(51) Int. Cl.
*G06F 15/00* (2006.01)

(52) U.S. Cl. .................................... 702/184

(58) Field of Classification Search ................. 702/184, 702/185; 600/301, 446; 714/37, 57; 707/104; 607/60
See application file for complete search history.

(56) References Cited

U.S. PATENT DOCUMENTS

| | | | |
|---|---|---|---|
| 2002/0129039 A1* | 9/2002 | Majewski et al. | 707/200 |
| 2003/0028226 A1* | 2/2003 | Thompson et al. | 607/60 |
| 2006/0149808 A1 | 7/2006 | Weiner et al. | |
| 2007/0124112 A1 | 5/2007 | Weyermann | |

\* cited by examiner

*Primary Examiner* — Bryan Bui
(74) *Attorney, Agent, or Firm* — Schiff Hardin LLP

(57) ABSTRACT

In a system and method to minimize downtimes of medical apparatuses one or more medical apparatuses each has at least: one detection module to detect error situations of the respective medical apparatus, one local database to provide data and information regarding error situations, associated error correction measures and additional information, one analysis module to analyze a present error situation with regard to measures for error correction and/or continued usability of the medical apparatus on the basis of the data stored in the local database, and one output module to output the results of the analysis. The apparatuses are connected with a central database in which data regarding known error situations of the medical apparatuses, associated error correction measures and additional information are provided. The local databases are updated on the basis of the central database. Given detection of a previously unknown error situation at an apparatus, the error situation is evaluated, error correction measures are established, additional information is compiled such as information regarding usability of the medical apparatus before implementation of the error correction measures, etc., the aforementioned data and information are provided to the central database, and the local databases are updated on the basis of the data of the central database.

21 Claims, 3 Drawing Sheets

FIG 2
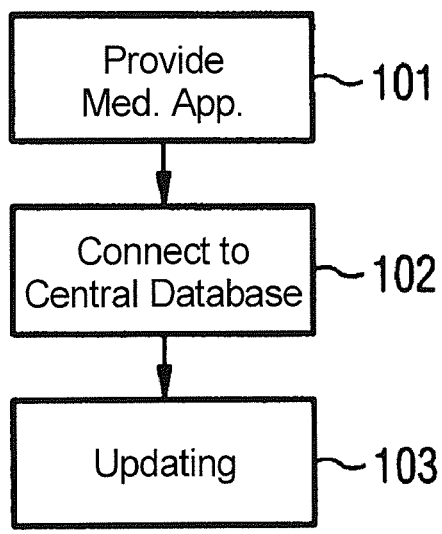
In the event that an unknown error situation is detected at an apparatus:
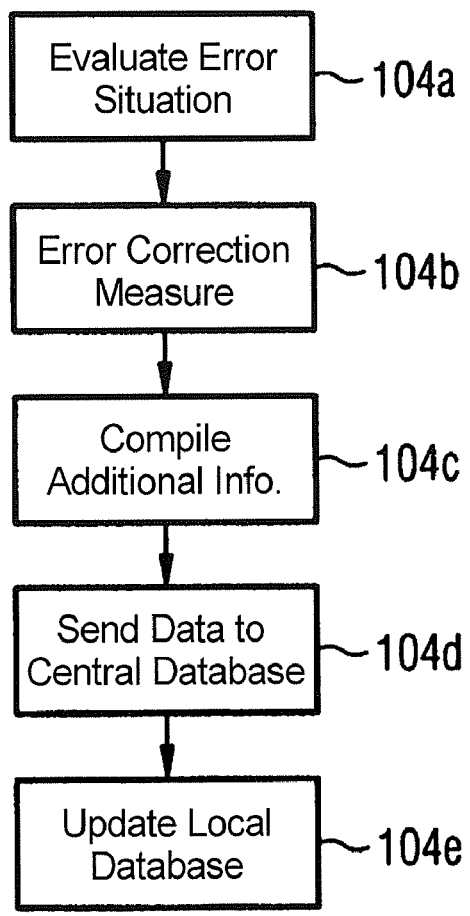

SYSTEM AND METHOD TO MINIMIZE DOWNTIMES OF MEDICAL APPARATUSES

BACKGROUND OF THE INVENTION

1. Field of the Invention

The present invention is in the field of medical technology and concerns a system and a method to minimize downtimes of medical apparatuses, in particular of imaging modalities such as computed tomography systems, MR apparatuses, radioscopy and acquisition systems, ultrasound apparatuses, etc.

2. Description of the Prior Art

As is known, technical systems or apparatuses of any type can fail or develop errors after a time period that cannot be individually predicted. Depending on the severity of the error that occurs, the systems or apparatuses are not at all affected in terms of their functionality, only slightly, or entirely. In the prior art, given the presence of an error situation, the user must initially make the decision as to whether the system or the apparatus can continue to be operated in spite of a (slight) error. In order to make this decision, the user must be able to estimate the degree of severity of the error situation. However, the user on site is typically not capable of correctly assessing error situations (in particular given complex technical apparatuses as are used in medical technology), such that the user overwhelmingly tends to not continue to use the medical apparatus given the occurrence of any error, but rather immediately requests a service technician. The medical apparatus therefore remains unused until the arrival of a service technician on site.

The called service technician inspects the malfunctioning medical apparatus (for example a CT apparatus) in order to obtain an impression of the current apparatus or error situation. Based on his or her experience, the technician then attempts to correct the error. In the event that this is not possible, the technician forwards a description of the error situation to a supervisory entity known as an uptime service center (USC). In the event that the USC cannot correct the error, the error is relayed to an entity known as a headquarter support center (HSC). In the event that the error still cannot be corrected here, the software or hardware development department of the manufacturer is called in order to analyze and correct the present error situation. Error situations that have previously occurred in user operation and their remedy are typically centrally known to the software or hardware development departments of the manufacturer, such that this knowledge is in principle available to the service technician. If a previously unknown (new) error situation occurs, this is analyzed on site by the service technician, described and transferred to the manufacturer, including a suggestion for error correction, an estimation of the effect of the error on the continued operation of the medical apparatus, and with data from the system log. An evaluation occurs at the manufacturer, with the result of the evaluation—for example the description of the error situation, the estimation of the effect of the error on the functionality and therefore the continued usability of the apparatus, the generation of instructions for error correction by the user, the generation of instructions for error correction and servicing to the service technician etc.— being centrally available at the manufacturer.

The previous procedure has proven to be disadvantageous for multiple reasons. It leads to long apparatus downtimes and in almost all error cases it requires the use of a service technician on site, which in turn incurs high costs. According to the conventional procedure, the risk also exists that it is easily possible that individual parameters with regard to the apparatus to be analyzed and/or the error situation to be analyzed are overlooked by the service technician, such that the technician possibly arrives at misinterpretations, which overall increases the risk of error.

SUMMARY OF THE INVENTION

An object of the present invention is to provide a system as well as a method for minimization of downtimes of medical apparatuses that remedies or at least significantly reduces the disadvantages of the prior art.

According to the invention, a system to reduce downtimes of medical apparatuses has one or more medical apparatuses that can be connected with a central database, each of the medical apparatuses including at least:
- one first module with which an error signal of the medical apparatus can be detected,
- one second module with a local database that contains data regarding error situations of the apparatuses, associated error correction measures and additional information,
- a third module with which an analysis with regard to error correction and/or continued usability of the medical apparatus can be conducted based on the detected error situation and the data stored in the local database, and
- a fourth module with which results of the analysis can be output.

Furthermore, data regarding all known error situations of the medical apparatuses, associated error correction measures and other associated information can be provided in the central database, wherein previously unknown error situations of a medical apparatus that are occurring for the first time can likewise be provided as corresponding data in the central database after their evaluation and assessment. The local databases can respectively be updated with the data of the central database.

The term "error situation" as used herein encompasses all parameters, data, information etc. that can be considered for an analysis of the respective medical apparatus. These data, parameters etc. can either be provided automatically by the apparatus or can be actively requested or determined by the first module (analysis module). Accesses to apparatus-specific instances (for example databases or configuration files) can likewise be executed. For example, the parameters can include a storage location on different drives, settings of the monitor, software error codes, settings in a registry, access right infractions, CPU performance values etc.

The system according to the invention embodies medical apparatuses that each have a local capability of error detection in a medical apparatus, the error analysis and the output of results of the error analysis, and instructions for error correction or for an additional method. For the error analysis and the error correction, data and information that are stored in the respective local database are accessed by the medical apparatus. These data encompass at least error situations, associated error correction measures and additional information. The error correction measures can require a manual intervention by the user or a service technician; they can ensue automatically by means of corresponding apparatus modules (for example software modules). In the latter case, an occurred error situation is automatically corrected by the apparatus. The "additional information" stored in the local database and the central database include at least conclusions and information about the effects of the detected error situation as to the functionality, and therefore as to the continued usability, of the medical apparatus. The user is hereby relieved of the difficult task of estimating the degree of severity of the error situation that has occurred.

So that the local databases each possess all current data and information regarding known error situations, their remedy, and information linked thereto, the local databases are connected with a (usually remote) central database. Due to this connection, for example a wired or wireless connection, data of the local databases can respectively be updated with data of the central database. The central database is operated by an operator, for example by the manufacturer of the medical apparatus or a service provider that is in charged of medical apparatuses of multiple manufacturers. The central database ideally contains all corresponding data and information regarding all previously occurred, known error situations of all medical apparatuses of the system. This can be ensured in that the operator of the central database is informed promptly after a new, previously unknown error situation becomes known, for example by the service technician, the manufacturer, the user, or even actively and automatically by the affected medical apparatus itself, and the error situation occurring for the first time as well as corresponding details/data for error correction and information at least about the possible impairments of the functionality of the medical apparatus are therefore promptly made available in the central database.

The system can have identical or different medical apparatuses, in particular imaging modalities such as CT apparatuses, MR apparatuses or ultrasound apparatuses. In principle, however, any medical apparatuses that has features and capabilities as described above come under consideration.

In one embodiment of the system, the detection of an error situation of the medical apparatus can be automatically or semi-automatically initiated with the first module. The first module can include a number of test modules that are designed for testing the apparatus, the test modules preferably being fashioned as software test modules. The test modules are automatically self-executing and can be fashioned as an executable file (executable), as a batch file, or as a Perl script. The test modules can be classified in different test groups. In a preferred embodiment, the following test groups are provided:

apparatus environment,
   apparatus configuration,
   safety,
   database,
   communication,
   information,
   additional test modules.

These groups can deviate from one another from apparatus type to apparatus type and can be expanded or modified at any time by additional test modules or additional groups.

In an embodiment of the system, at least the results of the analysis and the underlying error situation can be output with the fourth module in data form as a log file, and given the presence of an unknown error situation in the local database the log file can furthermore be automatically transferred to a central log file server. The log file server is advantageously positioned at the location of the central database.

In a further embodiment of the system, a fifth module with which the updating of the local databases can be initiated at predeterminable time intervals or given the presence of one or more predeterminable conditions is provided at the site of the central database. Alternatively or additionally, a sixth module with which the updating of the local database can be initiated given the presence of one or more predeterminable conditions can be provided at least at one medical apparatus of the system.

Furthermore, it is advantageous for the medical apparatuses to each have individual apparatus identifier from which at least the individual apparatus type can be derived. In a particularly advantageous embodiment, the local databases each contain only data and information that refer to the respective apparatus type.

In another particularly advantageous embodiment of the system, the updating of the local databases ensues only with data of the central database that correspond to the individual apparatus identifier of the respective medical apparatus.

The system according to the invention enables the local databases of the medical apparatuses belonging to the system to be supplied from a central database with current data and information regarding known error situations. For this purpose, the operator of the central database must ensure that new error situations occurring for the first time are evaluated and that at least one error correction and/or servicing instruction as well as details regarding effects on the customer operating instructions are made available as promptly as possible in the central database. In the event of the occurrence of a known error situation stored in the local database, the medical apparatuses can provide the user and/or a service technician with appropriate instructions for error correction and with regard to the degree of severity of the occurred error situation. If a service technician should be required to correct an error situation, corresponding instructions for error correction or handling can also be output specifically for a service technician.

Via instructions for the user to correct an error situation himself or herself, as well as via information regarding functionality of the medical apparatus in spite of a present error, the system contributes to significantly shorted downtimes of the medical apparatus. According to the principle underlying the system, the medical apparatuses increasingly "learn" to react to error situations. They provide the user with instructions of how he or she should respond given the presence of a given error situation, for example "call service technician and, if necessary, continue to work with power reductions", "call service technician and immediately discontinue the operation of the apparatus", or instructions of how the user can correct the error situation without a technician. This particularly applies for error situations that were not already known at the point in time of the delivery of the respective medical apparatus. The use of the system according to the invention also leads to a shortening of the deployment of the service technician since the medical apparatus immediately displays the instructions necessary for error correction by the service technician. The duration of the service deployment is therefore shortened.

The method according to the invention to reduce downtimes of medical apparatuses is characterized by the following method steps:

a) Provision of one or more medical apparatuses, wherein each apparatus has at least: one detection module to detect error situations of the respective medical apparatus; one local database to provide data regarding error situations, associated error correction measures and additional information; one analysis module to analyze a present error situation with regard to measures for error correction and/or continued usability of the medical apparatus on the basis of the data stored in the local database; one output module to output the results of the analysis.

b) Connection of the apparatuses with a central database in which data regarding known error situations of the medical apparatuses, associated error correction measures and additional information are provided.

c) Updating the local databases on the basis of the central database.

d) Given detection of a previously unknown error situation at an apparatus:
  d1) evaluation of the error situation,
  d2) establishment of corresponding error correction measures,
  d3) compilation of additional information such as, for example, information regarding usability of the medical apparatus before implementation of the error correction measures etc.,
  d4) provision of the data and information according to d1) through d3) to the central database and
  d5) updating the local databases on the basis of the data of the central database.

Similar or different imaging modalities such as CT apparatuses, MR apparatuses or ultrasound apparatuses can be provided as medical apparatuses in the method. The detection of the error situations by the detection modules is advantageously initiated automatically or semi-automatically. As mentioned in the preceding, the central database is typically located remote from the medical apparatuses, and the medical apparatuses can be connected with the central database via wired or wireless data connections or a data network.

In one embodiment of the method, the updating of the local databases is initiated at predeterminable time intervals. In a further embodiment of the method, the updating of the local database of a medical apparatus is initiated by the respective medical apparatus given the presence of one or more predeterminable conditions.

In an embodiment of the method, each medical apparatus has an individual apparatus identifier from which at least the individual apparatus type can be derived.

In a further embodiment of the method, the local databases each contain only data that relate to the respective apparatus type. In a further embodiment of the method, the local databases can be updated only with data of the central database that correspond to the individual apparatus identifier of the respective medical apparatus. The method steps d1) through d3) can be executed by one or more experts. Alternatively, intelligent software solutions that execute steps d1) through d3) can be used.

DESCRIPTION OF THE DRAWINGS

FIG. 2 schematically shows method steps of an embodiment the method according to the invention.

DESCRIPTION OF THE PREFERRED EMBODIMENTS

Figure 1:
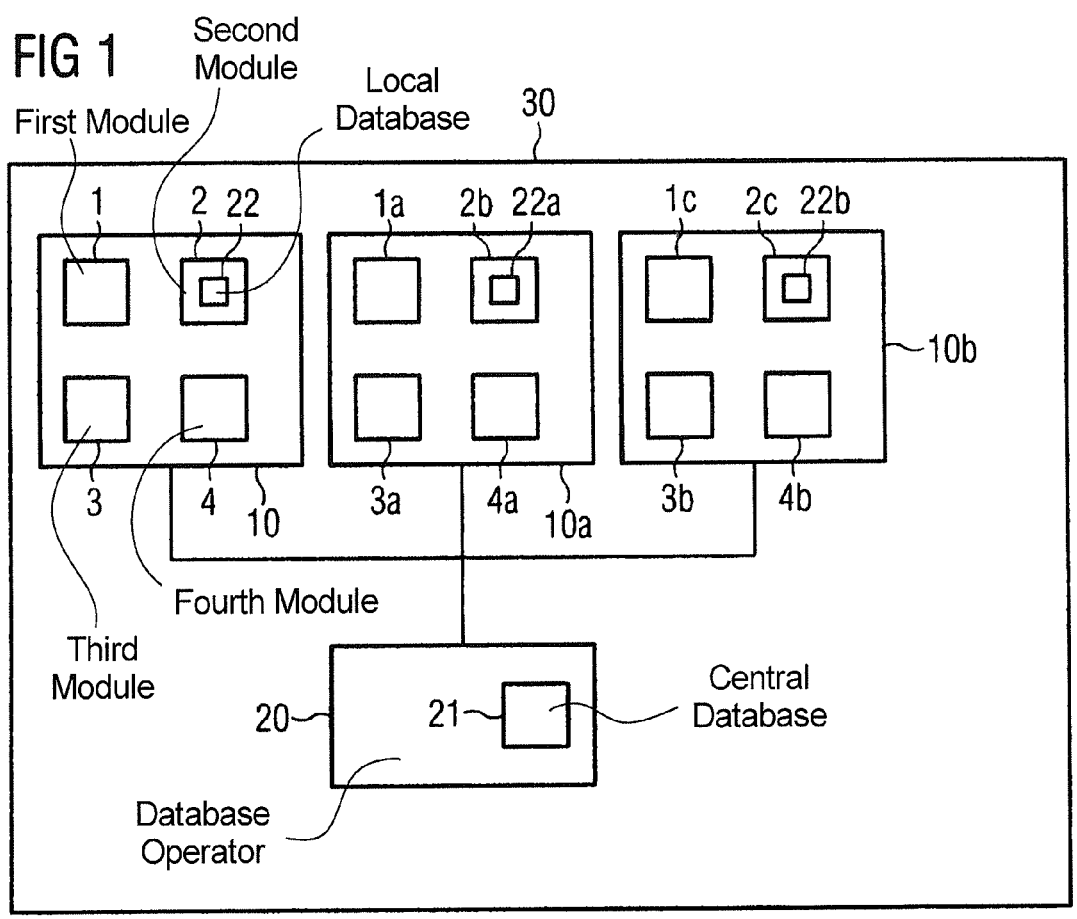
FIG. 1 schematically illustrates an embodiment of a system according to the invention.

FIG. 1 shows a schematic representation of a system 30 according to the invention to reduce downtimes of medical apparatuses, having three medical apparatuses 10, 10a, 10b connected with a central database 21. It is assumed that the three apparatuses are respectively CT apparatuses of the same model series. The CT apparatuses 10, 10a, 10b respectively have: a first module 1, 1a, 1b with which an error situation of the respective CT apparatus 10, 10a, 10b can be detected; a second module 2, 2a, 2b with a local database 22, 22a, 22b that contains data regarding error situations of the respective CT apparatus 10, 10a, 10b, associated error correction measures and additional information; a third module 3, 3a, 3b with which an analysis with regard to an error correction and/or a continued usability of the respective CT apparatus 10, 10a, 1b can be conducted based on the detected error situation and the data stored in the local database 22, 22a, 22b; and a fourth module 4, 4a, 4b with which results of the analysis can be output.

Data regarding all known, previously occurred error situations of the present CT apparatuses 10, 10a, 10b, associated error correction measures and other associated information are provided in the central database 21, wherein previously unknown error situations of a CT 10, 10a, 10b that are occurring for the first time are likewise available as corresponding data in the central database 21 after their evaluation and assessment. According to the invention, the local databases 22, 22a, 22b are respectively updated with the data of the central database 21.

FIG. 2 provides a schematic overview of the method according to the invention. The method according to the invention basically comprises the following three steps. In Step 101, a provision of one or more medical apparatuses 10, 10a, 10b ensues, wherein the medical apparatuses 10, 10a, 10b respectively have at least: a detection module 1, 1a, 1b to detect error situations of the respective medical apparatus 10, 10a, 10b; a local database 22, 22a, 22b to provide data and information regarding error situations, associated error correction measures and additional information; an analysis module 3, 3a, 3b for analysis of a present error situation with regard to measures for error correction and/or continued usability of the medical apparatus 10, 10a, 1b on the basis of the data stored in the local database 22, 22a, 22b; and an output module 4, 4a, 4b to output results of the analysis.

A connection of the medical apparatuses 10, 10a, 10b with a central database 21 in which data regarding known error situations of the medical apparatuses 10, 10a, 10b, associated error correction measures and additional information are provided ensues in Step 102.

An updating of the local databases 22, 22a, 22b on the basis of the data of the central database 21 ensues in Step 103.

If a previously unknown error situation that is not comprised in the local database is detected in a medical apparatus 10, 10a, 10b provided in Step 101, Steps 104a through 104e are then executed. An evaluation of the error situation ensues in Step 104a. A determination of corresponding error correction measures ensues in Step 104b. A compilation of additional information—for example information regarding usability of the medical apparatus 10, 10a, 10b before implementation of the error correction measures, etc.—ensues in Step 104c. In principle, Steps 104b and 104c can be implemented in one method step. A provision of the data and information according to Steps 104a through 104c to the central database 21 ensues in Step 104d. Updating of the local databases 22, 22a, 22b on the basis of the data of the central database 21 ensues in Step 104e.

Figure 3:
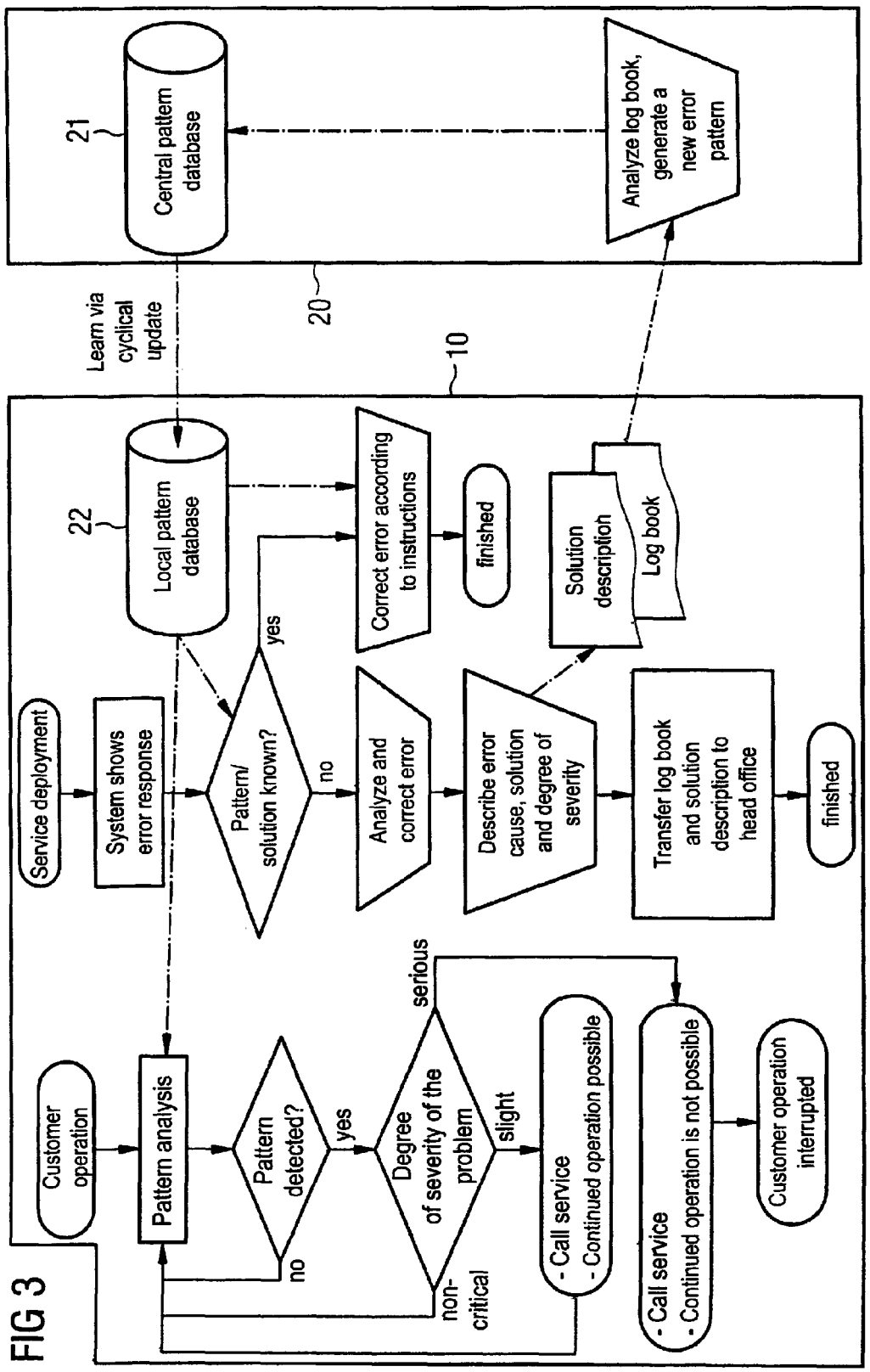
FIG. 3 shows an exemplary workflow diagram of the method according to the invention.

A schematic workflow scheme of the method according to the invention that is largely self-explanatory is shown in FIG. 3. Shown therein are method workflows that run in a system 30 that includes a medical apparatus 10 and a central database 21 connected thereto, the central database 21 being located at the manufacturer of the apparatus 10. The apparatus 10 has a local database 22 ("local pattern database"). The apparatus 10 can conduct a self-initiated error analysis at cyclically repeating time intervals. Alternatively, the apparatus 10 can also continuously execute a monitoring process in which an error analysis is conducted during the operation. Given the occurrence or detection of an error situation—designated in FIG. 3 as an (error) pattern—an analysis with regard to an error correction and/or a continued usability of the medical apparatus 10 runs in the apparatus 10 (more precisely in the third module 3) based on the detected error situation and the data stored in the local database 22. The decision tree that is to be executed can be seen at the left side of the image under the heading "customer operation", for example. Depending on the assessment of the degree of severity of the occurred error situation (the occurred problem) by the third module 3, the indicated instructions are output by the output unit 4 (not shown) of the apparatus 10. For example, the instructions "call service and continued operation is possible" is possible given a low degree of severity of the problem, or "call service and continued operation is not possible" given high degree of severity of the problem.

If the service technician is ultimately called because the user cannot independently conduct the error correction—such as if it is a new, previously unknown error, and therefore this error pattern cannot be stored in the local database and consequently the third module 3 cannot determine instructions for error correction or additional actions, or if the error is in fact known and stored in the local database 22 but the correction must be conducted by a service technician, the apparatus 10 assists the service technician on site insofar as it is a known error pattern stored in the local database 22. Corresponding instructions for error correction are thereby output to the service technician by the apparatus 10 on the basis of the data and information stored in the local database 22.

In the case of a new, previously unknown error pattern (=error situation), the service technician on site is initially, advantageously informed (via output of information, for example "unknown error pattern") by the affected medical apparatus 10 of the fact that this error pattern is not stored in the local database 22. In this case, the service technician can advantageously manually initiate an update of the local database 22 with data of the central database 21. The process of the analysis of the detected error pattern can subsequently be restarted. If the message "unknown error pattern" is thereupon output again, it is established that it is in fact a previously unknown error pattern or, respectively, an error pattern that has not previously occurred. In this case, the present error pattern is analyzed (either by the service technician, USC, HSC or the responsible development department of the manufacturer) and a corresponding instruction for error correction is generated. Furthermore, the degree of severity of the error is determined and a conclusion is drawn about the functionality of the apparatus 10 given the presence of this error. This information is transmitted to the operator 20 of the central database 21, who promptly stores these data and information in the central database 21. An active sending of the updated database data to the apparatus 10 advantageously ensues after storage of a newly-analyzed error situation, which sending is initiated by a fifth module (not shown) connected with the central database. Parallel to the transmission of the information to the operator 20, this information can be entered at least in part into a log book associated with the apparatus 10. This log book is typically continuously updated during the operation of the apparatus 10. In addition to confirmation messages, in particular warning and error messages of all active software components of the apparatus 10 are entered here. Alternatively or additionally, the log book or a section from this that covers the time period of the error situation is transferred to the operator 20 together with the error correction measures (proposed by the service technician, for example).

Although modifications and changes may be suggested by those skilled in the art, it is the intention of the inventors to embody within the patent warranted hereon all changes and modifications as reasonably and properly come within the scope of their contribution to the art.

We claim as our invention:

1. A system of medical apparatuses, said system comprising:
    a central database;
    one or more medical apparatuses, each medical apparatus comprising at least one first module configured to detect an error signal of the medical apparatus at which said first module is located, one second module comprising a local database that contains data, for the medical apparatus at which the second module is located, representing a record of previously occurring error situations of that medical apparatus, and that contains a record error correction procedures that have been undertaken for said error situations of that medical apparatus, and that contains information describing an effect of each error situation on functioning and continued usability of that medical apparatus, a third module configured to analyze a detected error situation at the medical apparatus at which the third module is located, dependent on the data in the local database in the second module at which the third module is located, to produce an analysis result comprising at least one of a procedure to correct the detected error situation and comprising an indication as to continued usability of the medical apparatus at which the third module is located, and a fourth module that emits said analysis result as an output;
    each local database being in communication with said central database to report all error situations and associated error correction procedures and continued usability of the medical apparatus to the central database, including error situations at the medical apparatus that have not previously occurred; and
    said central database being in communication with each local database to update the data in each local database.

2. A system as claimed in claim 1 wherein said one or more medical apparatuses comprise similar or different imaging modalities.

3. A system as claimed in claim 1 wherein said first module is configured to automatically or semi-automatically initiate detection of an error situation at the medical apparatus at which the first module is located.

4. A system as claimed in claim 1 wherein said central database is remote from said one or more medical apparatuses, and wherein said system comprises a communication link between said central database and each local database selected from the group consisting of data lines and a data network.

5. A system as claimed in claim 1 wherein said fourth module is configured to emit said analysis result as an output formulated as a log file, and wherein said fourth module, upon occurrence of an error situation that does not currently exist in the local database of the second module of the medical apparatus at which the fourth module is located, automatically transfers said log file to a central log file server.

6. A system as claimed in claim 5 wherein said central log file server is located at said central database.

7. A system as claimed in claim 1 wherein said central database comprises a fifth module configured to update each of said local databases at respective times selected from the group consisting of predetermined time intervals, and an occurrence of at least one predetermined condition.

8. A system as claimed in claim 7 wherein each of said one or more medical apparatuses comprises a sixth module configured to update the local database of the second module of the medical apparatus at which the sixth module is located, upon an occurrence of at least one predetermined condition.

9. A system as claimed in claim 1 wherein each of said one or more medical apparatuses comprises an apparatus identifier that identifies a type of that medical apparatus.

10. A system as claimed in claim 9 wherein each local database contains only data that refer to the apparatus type of the medical apparatus at which the local database is located.

11. A system as claimed in claim 9 wherein said central database is configured to detect said apparatus identifier and to update the local database at the medical apparatus having the apparatus identifier only with data relevant to the apparatus type that is identified by the apparatus identifier.

12. A method for operating a system of medical apparatuses, comprising the steps of:
providing one or more medical apparatuses and, at each medical apparatus, providing at least one detection module that detects error situations at that medical apparatus, one local database that provides data and information describing, for the medical apparatus at which the local database is located, a record of error situations, associated error correction procedures, and information describing functioning and continued use of the medical apparatus, one analysis module configured to analyze an occurring error situation with regard to procedures for error correction and/or continued usability of the medical apparatus dependent on data in the local database at that medical apparatus, and one output module that emits a result of the analysis as an output;
providing a communication link between each medical apparatus and a central database and, via the communication link, communicating data from each medical apparatus regarding known error situations and associated error correction procedures and additional information to the central database;
updating the respective local databases from the central database via each communication link; and
upon a detection at one of said medical apparatuses of an unknown error situation, (1) evaluating, at said one of said medical apparatuses, the unknown error situation, (2) establishing, at said one of said medical apparatuses, an error correction procedure for the unknown error situation, (3) compiling, in the local database of said one of said medical apparatuses, additional information regarding usability of said one of said medical apparatuses at which the unknown error situation occurred, or implementation of said error correction procedure, (4) providing data and information from steps (1) through (3) from said local database to the central database, and (5) updating each local database of all of said medical apparatuses dependent on data at the central database.

13. A method as claimed in claim 12 comprising providing similar or different imaging modalities as said one or more medical apparatuses.

14. A method as claimed in claim 12 comprising detecting said error situation with the detection module automatically or semi-automatically.

15. A method as claimed in claim 12 comprising locating said central database remote from the medical apparatus and communicating between said central database and each local database via a communication link selected from the group consisting of hardwired data connections, wireless data connections, and a data network.

16. A method as claimed in claim 12 comprising updating each local database from said central database at predetermined time intervals.

17. A method as claimed in claim 12 comprising initiating updating of each local database at the medical apparatus at which the local database is located, upon an occurrence of at least one predetermined condition.

18. A method as claimed in claim 12 comprising providing each medical apparatus with an apparatus identifier that identifies an apparatus type of that medical apparatus.

19. A method as claimed in claim 18 comprising storing data in each local database relating only to the apparatus type indicated by the apparatus identifier of that medical apparatus.

20. A method as claimed in claim 18 comprising updating each local database only with data that are relevant to the apparatus type of the apparatus identifier for the medical apparatus at which the local database is located.

21. A method as claimed in claim 12 comprising implementing steps (1) through (3) by at least one expert.

* * * * *